US007683213B2

(12) United States Patent
Dubois et al.

(10) Patent No.: US 7,683,213 B2
(45) Date of Patent: Mar. 23, 2010

(54) OXIDATION OF PROPANE TO GIVE ACRYLIC ACID USING CATALYSTS IN A MIXTURE OF CRYSTALLINE PHASES

(75) Inventors: Jean-Luc Dubois, Millery (FR); Manuel Baca, Villeurbanne (FR); Jean-Marc Millet, Lyons (FR)

(73) Assignee: Arkema, Puteaux (FR)

( * ) Notice: Subject to any disclaimer, the term of this patent is extended or adjusted under 35 U.S.C. 154(b) by 796 days.

(21) Appl. No.: 10/558,023

(22) PCT Filed: May 25, 2004

(86) PCT No.: PCT/FR2004/001290

§ 371 (c)(1), (2), (4) Date: Nov. 23, 2005

(87) PCT Pub. No.: WO2004/105938

PCT Pub. Date: Dec. 9, 2004

(65) Prior Publication Data

US 2006/0293538 A1 Dec. 28, 2006

(30) Foreign Application Priority Data

May 27, 2003 (FR) .................................. 03 06414

(51) Int. Cl.
*C07C 51/16* (2006.01)
(52) U.S. Cl. .................................... 562/547
(58) Field of Classification Search .................. 562/549
See application file for complete search history.

(56) References Cited

U.S. PATENT DOCUMENTS 6,143,916 A 11/2000 Hinago

FOREIGN PATENT DOCUMENTS

| EP | 0-608-838 A2 | 3/1994 |
| EP | 1-090-684 A1 | 11/2001 |
| EP | 1-254-710 A2 | 6/2002 |
| JP | 7-232071 | 9/1995 |
| JP | 10-330343 | 12/1998 |

OTHER PUBLICATIONS

Vallar, S. et M. Goreaud. "Structure Cristalline D'Une Forme Monclinique De TeMo5o16, Oxyde A Valence Mixte Conducteur Bidimensionnel." Journal of Solid State Chemistry: 129, pp. 303-307 (1997). Article No. SC967256.
Ekstrom, Thoimmy and Mats. "Ternary Phases With The Mo5O14 Type Of Structure." Acta Chemica Scandinavica: 26, pp. 182701835 (1972).
Millet, J. M. M., M. Baca, A. Pigamo, D. Vitry, W. Ueda and J. L. Dubois. "Study Of The Valence State And Coordination Of Antimony In MoVSbO Catalysts Determined By XANES And EXAFS." Applied Catalysis A: General: 244, pp. 259-270 (2003).
Plyasova, L. M., L. P. Solov'eva G. N. Krtyukova and T. V. Andrushkevich. "Study Of The Atomic Structure Of Vanadium-Molybdenum Catalysts For Oxidation Of Acrolein To Acrylic Acid." Kinetica i Kataliz: 31, pp. 1430-1434 (1990).
Kaddouri, A., R. Del Rosso, C. Mazzocchia, P. Gronchi and D. Fumagalli. "Isothermal Reduction Behaviour Of Some Metal Molybdates." Journal of Thermal Analysis and Calorimetry: 66, pp. 63-78 (2001).
Millet, J. M. M., H. Roussel, A. Pigamo, J. L. Dubois and J. C. Jumas. "Characterization Of Tellurium In MoVTeNbO Catalysts For Propane Oxidation Or Ammoxidation." Applied Catalysis A: General 232, pp. 77-92 (2002).

*Primary Examiner*—Kamal A Saeed
(74) *Attorney, Agent, or Firm*—Baker Botts LLP

(57) ABSTRACT

The invention relates to a method for the production of acrylic acid from propane, in which a gas mixture comprising propane, water vapour and, optionally, an inert gas and/or molecular oxygen is passed over a catalyst, comprising a crystalline catalyst phase of formula (I) or (I') TeaMo1VbNbcOx (I) Sba Mo1 VbOy (I'), associated with a crystalline catalyst phase for activating the propane.

9 Claims, 6 Drawing Sheets

Example 1

Example 2

Example 5

Example 6

Example 7

Example 8

Example 9

Example 10

Figure 1:
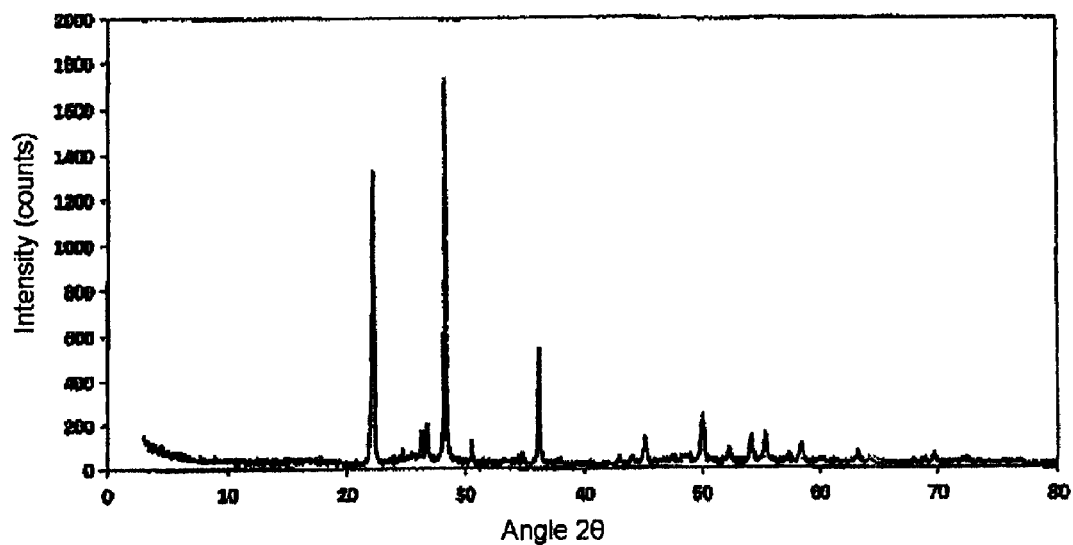

Diagram of the Pyrex reactor and the condensing system

OXIDATION OF PROPANE TO GIVE ACRYLIC ACID USING CATALYSTS IN A MIXTURE OF CRYSTALLINE PHASES

This application is a national phase of International Application Ser. No. PCT/FR04/001290, filed May 25, 2004, published Dec. 9, 2004, which claims priority to French Application 03/06414 filed May 27, 2003, each of which are incorporated by reference in their entireties herein, and from which priority is claimed.

The present invention relates to the selective oxidation of propane to acrylic acid, using catalysts in a mixture of crystalline phases, and the preparation of these catalysts.

The yield and selectivity of the preparation of acrylic acid from propane have often been rather limited, so that improvements are needed to increase the conversion of propane. The preparation of more active and more selective catalysts serves to remedy this problem.

Patent application JP 10-330343 describes catalysts useful for preparing nitrites by oxidation of an alkane in the gas phase. These catalysts with a crystalline structure are represented by the formula $Mo_aV_bSb_cX_xO_n$ and defined by their lattice parameters and diffraction angles (2θ). The symbol X denotes one or more metallic elements selected from Ti, Zr, Nb, Ta, Cr, W, Sn, etc. These catalysts are prepared by the addition of solutions or suspensions respectively containing an antimony source and a vanadium source, followed by the addition of a solution of suspension containing a specific quantity of molybdenum and addition of the element X in the powder or solution state. The oxides of these elements or derivatives, such as ammonium metavanadate or ammonium paramolybdate, are particularly preferred. The method leads to a precursor which is dried and calcined to give a compound of metal oxides. Two phases may be obtained during the preparation: an orthorhombic phase and a hexagonal phase. The orthorhombic phase is the anticipated phase. Catalyst performance can be improved by successive washings of the catalyst mixture obtained in order to obtain the orthorhombic phase alone.

Patent application JP 7-232071 describes catalysts having a crystalline structure corresponding to a formula of the MoV-TeX type. These catalysts are precalcined at 300° C. The X-ray diffraction lines indicated tend to imply the presence of an orthorhombic lattice structure.

European patent application EP-A-608838 describes the preparation of an unsaturated carboxylic acid from an alkane by a vapor phase catalytic oxidation in the presence of a catalyst containing a mixed metal oxide comprising Mo, V, Te and O as essential components, and at least one element selected from the group of niobium, tantalum, tungsten, titanium, aluminum, zirconium, chromium, manganese, iron, ruthenium, cobalt, rhodium, nickel, palladium, platinum, antimony, bismuth, boron, indium and cerium, these elements being present in clearly defined proportions.

European patent application EP-A-895809 and U.S. Pat. No. 6,143,916 describe oxide based catalysts comprising molybdenum, vanadium, niobium, oxygen, tellurium and/or antimony. These catalysts are used to convert propane to acrylic acid in the presence of molecular oxygen (examples 9 and 10 of the European application). Example 9 describes the oxidation of propane using a catalyst with the formula $Mo_1V_{0.33}Nb_{0.1}Te_{0.22}O_n$ from a gas stream comprising propane, oxygen and helium and a steam stream. U.S. Pat. No. 6,143,916 describes crystalline forms of these catalysts.

It has now been found, this being the object of the present invention, that the mixture of several different phases of catalysts in the crystalline state could yield surprising results for the oxidation of propane to acrylic acid, in comparison with the results obtained with catalysts comprising a single phase. It has in fact been demonstrated that the choice of the phases entering into the composition of the catalyst used is a very important factor.

According to the invention, a crystalline catalyst phase based on tellurium or antimony and molybdenum, preferably with a hexagonal lattice (referred to below as phase A) conferring the selectivity to the final mixture, in combination with a crystalline catalyst phase for activating the propane, can yield highly unexpected oxidation results from the standpoint of activity and selectivity. A synergistic effect can be observed in the use of the mixture of these crystalline catalyst phases.

The phase based on tellurium or antimony and molybdenum, conferring selectivity to the final mixture, can be selected advantageously from the compounds of tellurium and/or molybdenum or the compounds of antimony and molybdenum with a hexagonal lattice crystalline structure (phase A) or from $Te_2MoO_7$, or $Te_{0.2}MoO_x$.

The crystalline catalyst phase for conferring good selectivity either satisfies the formula:

$$Te_aMo_1V_bNb_cO_x \qquad (I)$$

or

$$Sb_{a'}Mo_1V_bO_y \qquad (I')$$

in which
a is between 0.1 and 2 limits included;
a' is between 0.1 and 2 limits included;
b is between 0 and 1 limits included;
c is between 0 and 0.2 limits included;
x and y represent the quantity of oxygen bound to the other elements and depends on their oxidation states, and corresponds to a hexagonal lattice structure of which the X-ray diffraction spectrum, diffraction angles (2θ) measured using the copper $K\alpha_1$ and $K\alpha_2$ lines of as an X-ray source, with a 0.02° step, has a peak at the diffraction angle 28.2° and lattice parameters a=0.729 (±0.02) nm×p, p being an integer from 1 to 4; c=0.400 (±0.01) nm×q, q being an integer from 1 to 2; α=90°, γ=120°, or has a monoclinic structure $Te_2MoO_7$ or $Te_{0.2}MoO_x$.

The crystalline catalyst phase for activating the propane is a phase of crystallized mixed metal oxides, more particularly based on molybdenum and vanadium, such as molybdenum-vanadium mixed oxides, such as a hexagonal phase catalyst (phase A) with antimony and niobium, or an orthorhombic phase catalyst (referred to below as phase B).

In particular, the crystalline phase for activating the propane satisfies the formulae (II), (II') or (II"):

$$MO_dV_eO_v \qquad (II)$$

$$MO_{d'}V_fSb_gNb_hO_w \qquad (II')$$

$$Mo_{d''}V_iTe_jNb_kO_z \qquad (II'')$$

in which
d, d' and d" are between 0.93 and 1 limits included;
e is between 0.05 and 1 limits included;
f is between 0 and 0.5 limits included;
g is between 0.05 and 0.3 limits included;
h is between 0.01 and 0.2 limits included;
is between 0 and 0.5 limits included;
j is between 0.05 and 0.3 limits included;
k is between 0.01 and 0.2 limits included;
v, w and z represent the quantity of oxygen bound to the other elements and depends on their oxidation states, it being understood that the product of formula (II') has either a hexagonal lattice structure in which the X-ray diffraction spectrum has a peak at the diffraction angle 28.2°, and lattice parameters a=0.729 (±0.02) nm×p, p being an integer from 1 to 4; c=0.400 (±0.01) nm×q, q being an integer from 1 to 2; $\alpha=90°$, $\gamma=120°$, or has an orthorhombic lattice structure in which the X-ray diffraction spectrum has a peak at the diffraction angle 27.3° and lattice parameters a=2.68 (±0.04) nm; b=2.12 (±0.04) nm; c=0.401 (±0.006) nm×q', q' being an integer from 1 to 2; $\alpha=\beta=\gamma=90°$, and it being understood that the product of formula (II") has an orthorhombic lattice structure and also has an X-ray diffraction peak at the diffraction angle 27.3° and lattice parameters a=2.68 (±0.04) nm; b=2.12 (±0.04) nm; c=0.401 (±0.006) nm×q', q' being an integer from 1 to 2; $\alpha=\gamma=90°$.

In the X-ray diffraction spectra of the above hexagonal or orthorhombic crystalline structures, the diffraction angles (2θ) are measured using the copper $K\alpha_1$ and $K\alpha_2$ lines as an X-ray source, with a step of 0.02°.

According to a preferred embodiment of the invention, the combination of crystalline catalyst phases is prepared in ratios from 90/10 to 15/85 by weight of the total weight of mixture, of the catalyst conferring good selectivity/catalyst for activating the propane, preferably 90/10 to 50/50 by weight of the total weight of mixture, and particularly preferred, from 70/30 to 50/50 by weight of the total weight of mixture, of the catalyst conferring good selectivity/catalyst for activating the propane.

Thus in particular, in the combination of catalysts, it is advantageous to use 10 to 50% by weight of the crystalline catalyst phase for activating the propane, preferably 30 to 50% by weight.

A subject of the present invention is a method for preparing acrylic acid from propane, in which a gas mixture comprising propane, steam and, optionally, an inert gas and/or molecular oxygen, is passed over a catalyst for conferring good selectivity for acrylic acid, of formula (I), (I'), $Te_2MoO_7$ or $Te_{0.2}MoO_x$ combined with a crystalline catalyst phase for activating the propane.

Preferably, the method according to the present invention consists in passing the above gas mixture over a catalyst comprising a combination of a catalyst with formula (I), (I'), $Te_2MoO_7$ or $Te_{0.2}MoO_x$ and a crystalline catalyst phase of formula (II), (II') or (II").

According to a preferred embodiment of the invention, acrylic acid is prepared from propane using a catalyst comprising a combination of crystalline phases in ratios from 90/10 to 15/85 by weight of the total weight of mixture, of the catalyst conferring good selectivity/catalyst for activating the propane, preferably 90/10 to 50/50 by weight, and particularly preferred, from 70/30 to 50/50 by weight of the total weight of mixture, of the catalyst conferring good selectivity/catalyst for activating the propane.

Preferably, according to the method of the present invention, when operating in the presence of molecular oxygen, the propane/molecular oxygen molar ratio in the initial gas mixture is equal to or greater than 0.5. A molecular ratio equal to or greater than 0.3 may also be advantageous.

The present invention further relates to the use of a combination of catalysts with a crystalline structure of formula (I), or (I'), $Te_2MoO_7$ or $Te_{0.2}MoO_x$ with catalysts of a crystalline structure of formulae (II), (II') or (II") for activating the propane, for preparing acrylic acid from propane.

The method according to the invention simultaneously provides good selectivity for acrylic acid and a high propane conversion. Furthermore, it can be implemented easily in a fixed bed, fluidized bed or moving bed, and the reactants can be injected into the reactor at various points, so that the operation remains outside the flammability zone while producing a high propane concentration, and in consequence, high catalyst productivity. The unconverted propane can be recycled.

According to a particularly advantageous embodiment, the method according to the invention comprises the following steps:

I/ In the Absence of Molecular Oxygen

If the initial gas mixture contains no molecular oxygen, the propane is oxidized by the following redox reaction (A):

II/ In the Presence of Molecular Oxygen
  a) the initial gas mixture is introduced into a reactor with a moving catalyst bed;
  b) the gases are separated from the catalyst at the outlet of the first reactor;
  c) the combination of catalysts is sent to a regenerator; and
  d) the regenerated catalyst issuing from the regenerator is reintroduced into the reactor.

According to another advantageous embodiment of the invention, the method comprises the repetition, in a reactor provided with the combination of catalysts, of the cycle comprising the following successive steps:
  1) injection of the gas mixture as previously defined;
  2) injection of steam and, if applicable, inert gas;
  3) injection of a mixture of molecular oxygen, steam and, if applicable, inert gas; and
  4) injection of steam and, if applicable, inert gas.

It is understood that step 1) can be carried out in the form of multiple injections.

According to an improvement of the advantageous embodiment just described, the cycle comprises an additional step that precedes or follows step 1) and during which the gas mixture corresponding to that of step 1) is injected, but without molecular oxygen, the propane/molecular oxygen molar ratio then being calculated on the whole for step 1) and this additional step.

According to an advantageous embodiment of the improvement just described, the additional step precedes step 1) in the cycle.

Other features and advantages of the invention are described in greater detail below.

DETAILED DESCRIPTION OF THE METHOD OF THE INVENTION

According to the invention, in the alternatives in which molecular oxygen is introduced, since the propane/molecular oxygen molar ratio in the initial gas mixture is preferably equal to or greater than 0.5 or equal to or greater than 0.3, the conversion of propane to acrylic acid using the catalyst is carried out by oxidation, probably by the following competing reactions (A) and (B):

the conventional catalytic reaction (B):

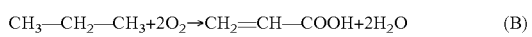

and the redox reaction (A) mentioned above:

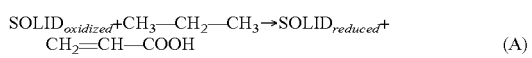

The propane/steam volume ratio in the initial gas mixture is not critical and may vary within wide limits.

Similarly, the proportion of inert gas, which may be helium, krypton, a mixture thereof, or nitrogen, carbon dioxide, etc., is also not critical and may also vary within wide limits.

The proportions of the components of the initial gas mixture are generally as follows (in molar ratios):

propane/oxygen/inert gas (He—Kr)/$H_2O$ (steam)=1/0.05-2/1-10/1-10 or preferably 1/0.5-2/1-10/1-10

Even more preferably, they are 1/0.1-1/1-5/1-5.

Even more preferably they are 1/0.167-0.667/2-5/2-5. The following proportions are also particularly advantageous: 1/0.2-0.4/4-5/4-5.

In general, reactions (A) and (B) are conducted at a temperature of between 200 and 500° C., preferably between 250 and 450° C., even more preferably between 350 and 400° C. The pressure in the reactor or reactors is generally $1.01 \times 10^4$ to $1.01 \times 10^6$ Pa (0.1 to 10 bar), preferably $5.05 \times 10^4$ to $5.05 \times 10^5$ Pa (0.5-5 bar).

The residence time in the reactor is generally between 0.01 and 90 seconds, and preferably between 0.1 and 30 seconds.

Preparation of Catalysts

The crystallized catalysts of formulae (I), (I'), $Te_2MoO_7$ or $Te_{0.2}MoO_x$ or formulae (II), (II'), (II") can be prepared by various methods, such as hydrothermal synthesis, coprecipitation or solid-solid reaction.

Some of them can be prepared in particular by the methods described in U.S. Pat. No. 6,143,916, in Japanese patent application JP 10-330343, in J. of Solid State Chemistry, 129, 303 (1997); Acta Chemica Scandinavica, 26, 1827 (1972); Applied Catalysis, A: General, 244, 359-70 (2003); or described by L. M. Plyasova et al, Kinetica i Kataliz, 31(6), 1430-1434 (1990); by A. Kaddouri et al, J. Therm. Anal. Cal, 66, 63-78 (2001); by J. M. M. Millet et al, Appl, Catal., 232, 77-92 (2202). They can also be prepared as described below in the examples.

In general, the sources of the various metals used as raw materials are often oxides, but are not necessarily limited to oxides. In a nonlimiting manner, the following raw materials can be used:

in the case of molybdenum, ammonium molybdate, ammonium paramolybdate, ammonium heptamolybdate, molybdic acid, molybdenum halides and oxyhalides such as $MoCl_5$, organometallic compounds of molybdenum such as molybdenum alkoxides such as $Mo(OC_2H_5)_5$, acetylacetone molybdenyl;

in the case of tellurium, the tellurium, telluric acid, $TeO_2$;

in the case of antimony, for example, antimony oxide (antimony trioxide), particularly the senarmontite variety, antimony sulfate $(Sb_2(SO_4)_3)$ or an antimony chloride (an antimony trichloride, antimony pentachloride);

in the case of vanadium, ammonium metavanadate, vanadium halides and oxyhalides such as $VCl_4$, $VCl_5$ and $VOCl_3$, organometallic compounds of vanadium such as vanadium alkoxides such as $VO(OC_2H_5)_3$;

in the case of niobium, niobic acid, niobium tartrate, niobium hydrogenoxalate, ammonium oxotrioxalate niobiate $\{(NH_4)_3[NbO—(C_2O_4)_3], 1.5H_2O\}$, niobium ammonium oxalate, niobium oxalate or tartrate, niobium halides or oxyhalides such as $NbCl_3$, $NbCl_5$ and organometallic compounds of niobium such as niobium alkoxides such as $Nb(OC_2H_5)_5$, $Nb(O$-n-$Bu)_5$;

and, in general, all compounds suitable for forming an oxide by calcination, that is, metal salts of organic acids, metal salts of inorganic acids, complex metallic compounds, etc.

One mode for preparing catalysts consists in mixing, with stirring, aqueous solutions of niobic acid, oxalic acid, and ammonium heptamolybdate, ammonium metavanadate, telluric acid or antimony oxide, and preferably precalcining the mixture in air at about 300-320° C., and calcining under nitrogen at about 600° C.

According to a preferred embodiment, one method for preparing catalysts consists in preparing a solution of niobic acid and oxalic acid, preparing a solution of molybdenum, vanadium, tellurium or antimony, mixing the two solutions to form a gel, followed by drying of the gel obtained, precalcination and calcination.

According to a particularly preferred method, the catalyst can be prepared by the following steps:

1) dissolution in water of a vanadium source, for example, ammonium metavanadate, with stirring and, optionally, heating;

2) if applicable, addition to the above solution of a source of tellurium or antimony, for example, telluric acid, or antimony oxide (particularly the senarmontite variety);

3) addition of a molybdenum source, for example ammonium heptamolybdate;

4) reaction of the solution obtained, under reflux;

5) if applicable, addition of an oxidant such as hydrogen peroxide in the case of antimony catalysts;

6) if applicable, addition of the solution prepared by mixing, with heating, a niobium source, for example niobic acid, with oxalic acid;

7) reaction of the reaction medium under reflux and preferably under inert atmosphere, until a gel is obtained;

8) drying of the gel obtained;

9) preferably, precalcination of this gel; and 10) calcination of the gel, precalcined if necessary, to obtain the catalyst.

In the alternatives to the above methods:

drying [for example in step 8)] can be carried out in an oven as a thin layer, by spray drying, by freeze drying, by zeodration, by microwaves, etc;

precalcination can be carried out under air flow at 280-300° C. or under static air at 320° C., in fluidized bed, in a rotary furnace in an aerated fixed bed, so that the catalyst particles are separated from one another to prevent them from joining during precalcination or possibly during calcination;

calcination is preferably carried out under very pure nitrogen and at a temperature close to 600° C., for example in a rotary furnace or in a fluidized bed and for a period of up to 2 hours.

According to a particularly preferred embodiment of the invention, precalcination is carried out:

either at a temperature below 300° C. under an air flow of at least 10 ml/min/g of catalyst;

or at a temperature of between 300 and 350° C. under an air flow of less than 10 ml/min/g of catalyst.

According to a particularly preferred embodiment, precalcination is carried out:

at about 320° C. under an air flow of less than 10 ml/min/g; or at about 290° C., under an air flow of about 50 ml/min/g.

According to another method for preparing catalysts, a solid-solid reaction is carried out by mixing the metal sources followed by co-grinding to obtain a uniform mixture. The solid is obtained after heating under reduced pressure at a temperature close to 600° C.

Advantageously, metal oxides or the metal itself are used as the metal source. Preferably, the heating is carried out for a prolonged period (preferably 3 days to 1 week).

The catalysts prepared by the methods described above may each be produced in the form of particles generally from 20 to 300 microns in diameter, the particles of each of the combined catalysts generally being mixed before carrying out the method according to the invention. The particles can be obtained by spray-drying a gel or a suspension.

The combination of catalysts may also be in the form of a solid catalytic composition comprising particles each of which comprises both of the catalysts.

Catalyst Regeneration

During the redox reaction (A), the catalysts undergo a reduction and a progressive loss of their activity. When the catalysts are at least partially in the reduced state, they are regenerated by the reaction (C):

$$SOLID_{reduced} + O_2 \rightarrow SOLID_{oxidized} \quad (C)$$

by heating in the presence of oxygen or a gas containing oxygen at a temperature of 250 to 500° C., for the time necessary to reoxidize the catalysts.

The proportions of the components of the regeneration gas mixture are generally as follows (in molar ratios):

oxygen/inert gas (He—Kr)/$H_2O$ (steam)=1/1-10/0-10 Preferably, they are 1/1-5/0-5.

Instead of using oxygen alone, dry air (21% $O_2$) can be used. Instead of or in addition to steam, moist air can be used.

The regeneration temperature is generally 250 to 500° C.

The method is generally carried out until the catalyst reduction rate is between 0.1 and 10 g of oxygen per kg of catalyst.

This reduction rate can be monitored during the reaction by the quantity of products obtained. The equivalent quantity of oxygen is calculated. It can also be monitored by the exothermicity of the reaction. The reduction rate can also be tracked by the quantity of oxygen consumed in the regenerator.

After regeneration, which can be carried out under temperature and pressure conditions identical to or different from those of reactions (A) and (B), the catalysts recover an initial activity and can be reintroduced into the reactor.

Reactions (A) and (B) and regeneration (C) can be carried out in a conventional reactor, such as a fixed bed reactor, a fluidized bed reactor, or a moving bed reactor.

Thus, reactions (A) and (B) and regeneration (C) can be carried out in a two-stage device, that is, a reactor and a regenerator which operate simultaneously, and in which two feeds of the catalyst combination alternate periodically.

Reactions (A) and (B) and regeneration (C) can also be carried out in the same reactor, by alternating the reaction and regeneration periods.

Preferably, reactions (A) and (B) and regeneration (C) are carried out in a moving catalyst bed reactor, particularly in a vertical reactor, with the catalyst preferably moving upward.

An operating mode with a single pass of the gases or with gas recycling can be used.

According to a preferred embodiment, the propylene produced and/or the unreacted propane are recycled (or returned) to the reactor inlet, that is, they are reintroduced at the reactor inlet, in a mixture or in parallel with the initial mixture of propane, steam and, optionally, inert gas(es).

The present invention has the great advantage of combining very good selectivity for acrylic acid and good propane conversion, because of the combination of catalysts employed and the synergistic effect procured. In this synergistic effect, it may be observed, on the one hand, that each catalyst considered separately is less efficient than the combination of the catalyst for procuring good selectivity with the catalyst for activating the propane and, on the other hand, that the selectivity observed is higher than the additive effect procured by the two catalysts considered separately, in nearly all cases. This effect can be observed in particular in the tests discussed below.

EXAMPLES

The following examples illustrate the present invention but without limiting its scope.

In the examples below, the selectivities and the propane conversion are defined as follows:

$$\text{Propane Conversion}(\%) = \frac{\text{Number of moles of propane reacted}}{\text{Number of moles of propane introduced}} \times 100$$

$$\text{Acrylic acid selectivity}(\%) = \ldots \frac{\text{Number of moles of acrylic acid formed}}{\text{Number of moles of propane reacted}} \times 100$$

The selectivities relative to the other compounds are calculated similarly.

Preparation of Pure Catalyst Phases

Example 1

Preparation of Phase A with Tellurium of Composition $MoV_{0.8}Te_{0.6}O_x$

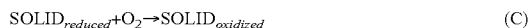

The preparation was made by solid-solid reaction in an under vacuum sealed ampoule. 10.00 g of $MoO_3$ (Merck), 1.37 g of molybdenum metal (Alfa Aesar), 8.01 g $TeO_2$ (Alfa Aesar) and 3.04 g $V_2O_5$ (Riedel de Haën) were ground together in an agate mortar for 15 minutes, until a uniform mixture was obtained. This mixture was introduced into a quartz ampoule. The ampoule was then sealed under vacuum and heated at 600° C. for one week. The solid recovered was analyzed by X-ray diffraction. The analysis confirmed the production of the desired phase, which corresponded to the hexagonal structure (diffraction diagram—FIG. 1). The solid obtained had the chemical formula: $MoV_{0.8}Te_{0.6}O_x$, where x is the quantity of oxygen corresponding to the oxidation state of the cations.

Example 2

Preparation of Phase A with Tellurium and Niobium of Composition $MoV_{0.3}Te_{0.4}Nb_{0.1}O_x$ Phase A with tellurium containing niobium was obtained by coprecipitation. 5.00 g of ammonium heptamolybdate (Starck)+1.00 g of ammonium metavanadate (GFE)+2.60 g of telluric acid (Fluka)+25 ml of water were introduced into a beaker. The beaker was heated (70° C.) with stirring until a clear solution was obtained. Simultaneously, 0.52 g of niobic acid (CBMM)+1.08 g of oxalic acid (Alfa Aesar)+15 ml of water were introduced into a beaker. The beaker was heated until the solution became clear (about 4 hours, temperature 70° C.), the solution was centrifuged (3500 rpm for 15 minutes) and the liquid phase was added to the solution containing Mo, V and Te. This produced an orange gel that was placed overnight in the oven at 110° C. The solid obtained was precalcined in air for 4 hours at 300° C. (50 ml/min/g) and calcined for 2 hours at 600° C. under nitrogen (50 ml/min/g).

Figure 2:
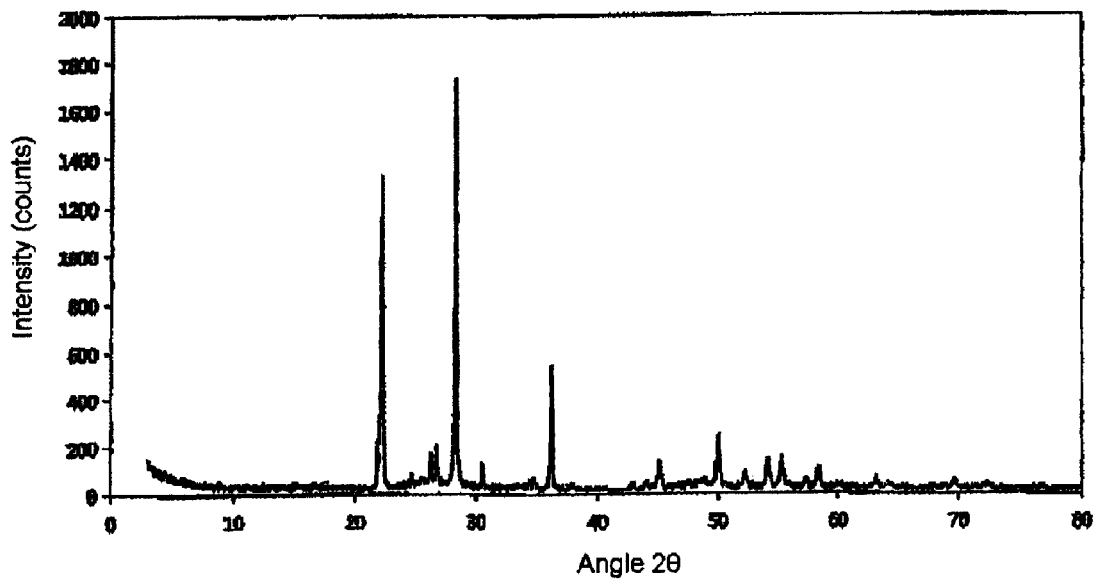

The solid obtained had the chemical formula: $MoV_{0.3}Te_{0.4}Nb_{0.1}O_x$. The solid recovered was analyzed by X-ray diffraction (FIG. 2).

Example 3

Preparation of Phase A with Antimony of Composition $Mo_1V_{0.5}Sb_{0.3}O_y$.

Figure 3:
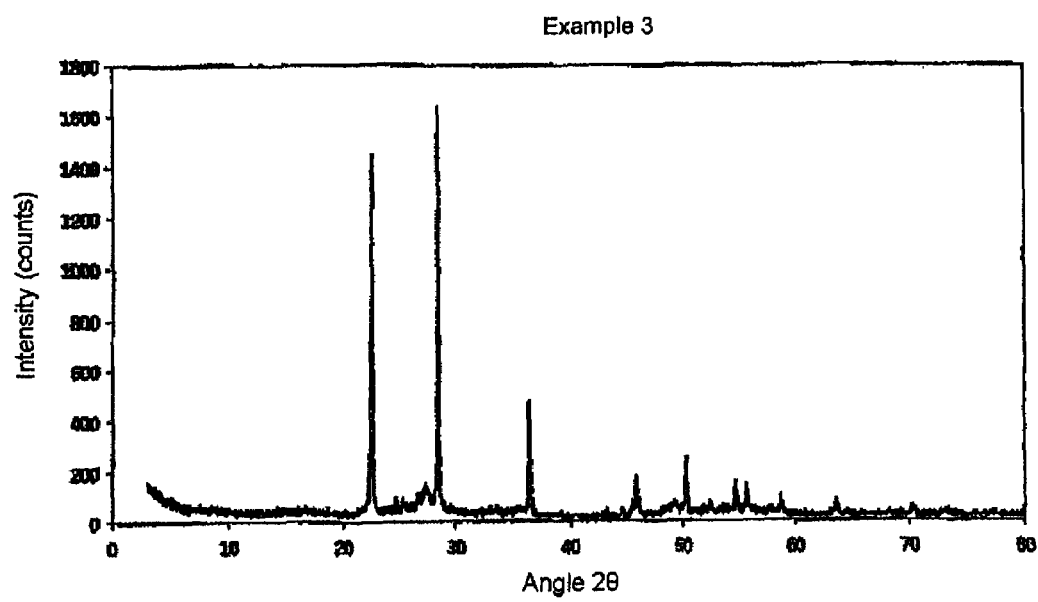

Phase A with antimony was prepared like the one in example 1, but with the following components, 15.00 g of $MoO_3$ (Merck)+5.49 g $Sb_2O_3$+2.85 g of $V_2O_5$ (Riedel de Haën)+2.05 g Mo (Alfa Aesar) were ground for 15 minutes in an agate mortar and introduced into an ampoule. The ampoule was sealed under vacuum and heated at 600° C. for one week. The solid obtained had the chemical formula: $Mo_1V_{0.5}Sb_{0.3}O_y$. The solid recovered was analyzed by X-ray diffraction (FIG. 3).

Example 4

Preparation of Phase A with Antimony and Niobium of Composition $MoV_{0.3}Sb_{0.1}Nb_{0.1}O_w$.

Phase A with antimony containing niobium was obtained by coprecipitation. 7.00 g of ammonium heptamolybdate (Starck)+1.39 g of ammonium metavanadate (GfE) were introduced into a beaker, heated (80° C.) with stirring until a clear solution was obtained. 1.17 g of $Sb_2O_3$ (Alfa Aesar) was then added and the mixture stirred for four hours with continued heating. 2 ml of $H_2O_2$ containing 30% by weight (Alfa Aesar) diluted in 10 ml of water was then added, and the solution then turned a clear orange color.

Simultaneously, 0.66 g of niobic acid (CBMM)+1.34 g of oxalic acid (Alfa Aesar)+15 ml of water were introduced into a beaker. The mixture was heated until the solution became clear (about 4 hours, temperature 70° C.), and then centrifuged (3500 rpm for 15 minutes) and the liquid phase was then added to the solution containing Mo, V and Sb. This produced a yellow gel that was left overnight in the oven at 110° C. The solid obtained was precalcined in air for 4 hours at 300° C. (50 ml/min/g) and calcined for 2 hours at 600° C. under nitrogen (50 ml/min/g). The solid obtained had the chemical formula: $MoV_{0.3}Sb_{0.1}Nb_{0.1}O_w$.

Figure 4:
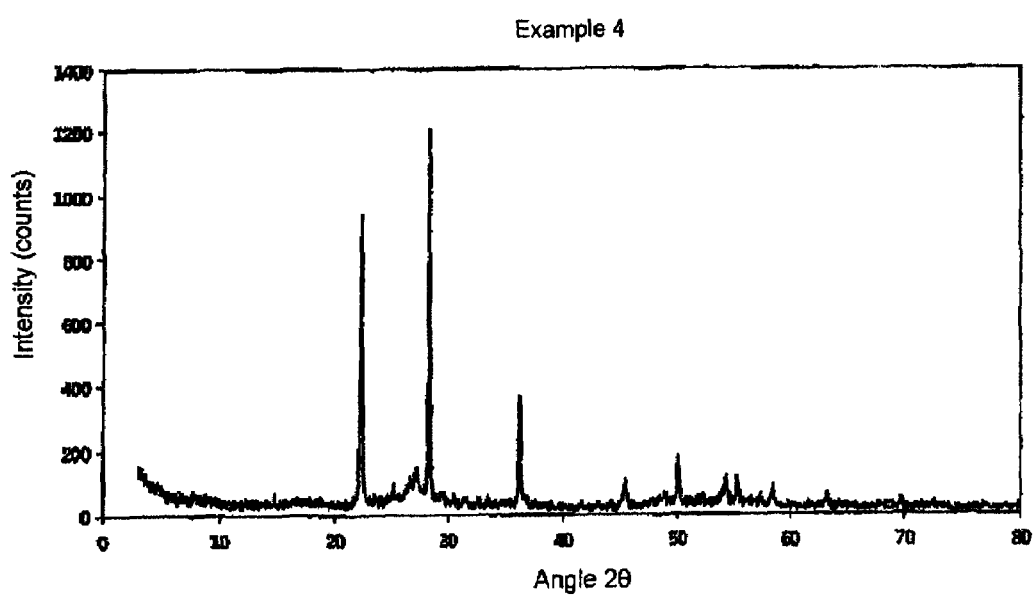

The solid recovered was analyzed by X-ray diffraction (FIG. 4).

Example 5

Preparation of a Phase with Molybdenum of the $V_{0.95}Mo_{0.97}O_5$ Type

Figure 5:
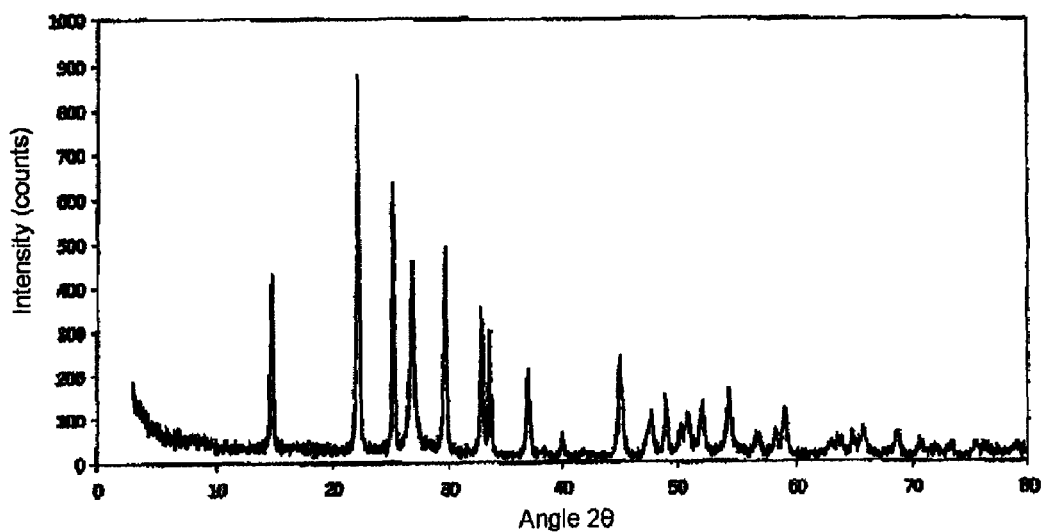

The $V_{0.95}Mo_{0.97}O_5$ phase was prepared by hydrothermal synthesis. 2.00 g of ammonium heptamolybdate (Starck), 1.33 g $VOSO_4$ (Alfa Aesar) and 0.07 g of $NH_4OH$ (28% by weight $NH_3$) were introduced with 50 ml of water into a 100 ml Teflon jar. The mixture was left for 72 hours at 175° C. in an autoclave. The solid was then filtered, washed with distilled water, dried in the oven at 110° C. and calcined under nitrogen at 600° C. for 2 hours (50 ml/min/g). The solid obtained had a chemical formula of the $Mo_1V_1O_y$ type. The solid recovered was analyzed by X-ray diffraction (FIG. 5), and conformed to JCPDS (Joint Committee of Powder Diffraction Spectroscopy) datasheet 77-0649. This phase has been described by L. M. Plyasova et al, Kinetica i kataliz, 31(6), 1430-1434 (1990).

Example 6

Preparation of a Phase with Tellurium and Molybdenum of the $Te_2MoO_7$ Type

Figure 6:
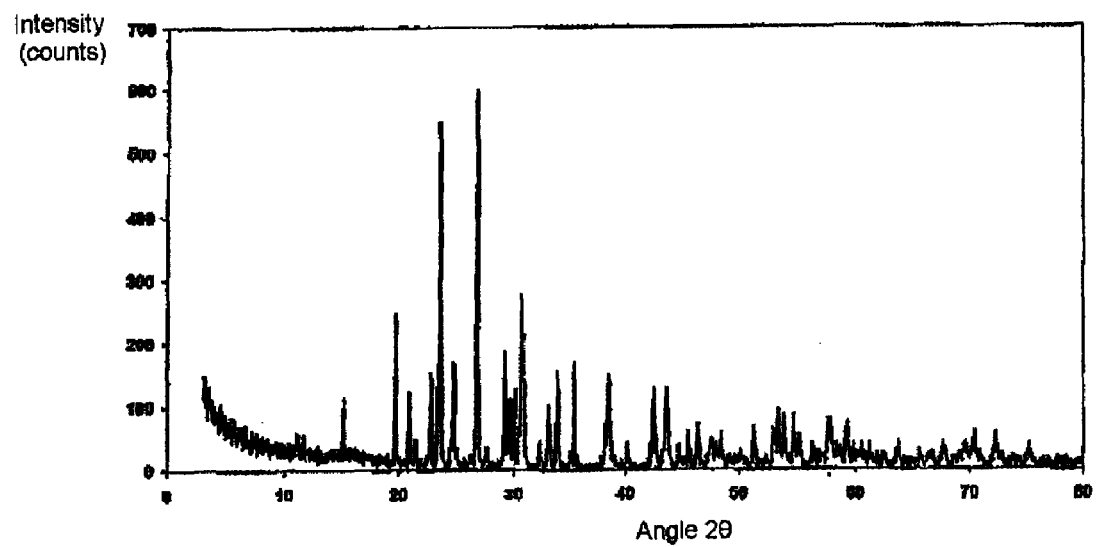

The $Te_2MoO_7$ phase was prepared by coprecipitation. 6.50 g of telluric acid (Fluka) and 2.50 g ammonium heptamolybdate (Starck) were dissolved in a minimum of water (15 ml). The mixture was heated (80° C.) with stirring and allowed to evaporate to a white paste that was left to dry overnight in the oven at 110° C. The solid obtained was calcined for 2 hours at 470° C. in air (50 ml/mm/g). The solid obtained had the chemical formula of $Mo_{0.5}Te_1O_x$. The solid recovered was analyzed by X-ray diffraction (FIG. 6) and conformed to JCPDS datasheet 70-0047. This phase has been described by A. Kaddouri et al, J. Therm. Anal. Cal., 66, 63-78 (2001).

Example 7

Preparation of a Phase with Tellurium and Niobium of Composition: $Mo_1V_{0.26}Te_{0.10}Nb_{0.14}O_2$ MoVTeNb catalyst containing a high concentration of phase B. The following were introduced simultaneously into a 100 ml beaker: 35 ml of distilled water+7.78 g of ammonium heptamolybdate (Starck)+1.70 g of ammonium metavanadate (GfE)+2.22 g of telluric acid (Fluka). The mixture was heated at 80° C. with stirring to obtain a clear red solution. The solution was then left to cool at ambient temperature.

A solution of niobic acid/oxalic acid with an oxalate/Nb ratio of 2.70 was prepared simultaneously. The following were introduced into a 50 ml beaker: 10 ml of distilled water+ 0.82 g of niobic acid (CBMM)+1.67 g of oxalic acid (Alfa Aesar). The mixture was heated at 70° C. with stirring until the initial solution became clear (about 4 hours). The solution was centrifuged (3500 rpm for 15 minutes) and the liquid phase was then introduced into the clear red solution containing the molybdenum, vanadium and tellurium. After a few minutes, an opaque orange gel was obtained, and was placed in a crystallizer for drying overnight in the oven at 110° C. The solid was precalcined in air at 300° C. for 4 hours (50 ml/min/g) and then calcined in purified nitrogen at 600° C. for two hours (50/ml/min/g).

The solid recovered was analyzed by X-ray diffraction. This showed a mixture of hexagonal phase and the desired orthorhombic phase. The solid obtained had the chemical formula $Mo_1V_{0.26}Te_{0.10}Nb_{0.14}O_z$ and had a diffraction diagram similar to the one described by J. M. M. Millet et al, Appl. Catal., 232 77-92 (2002).

Figure 7:
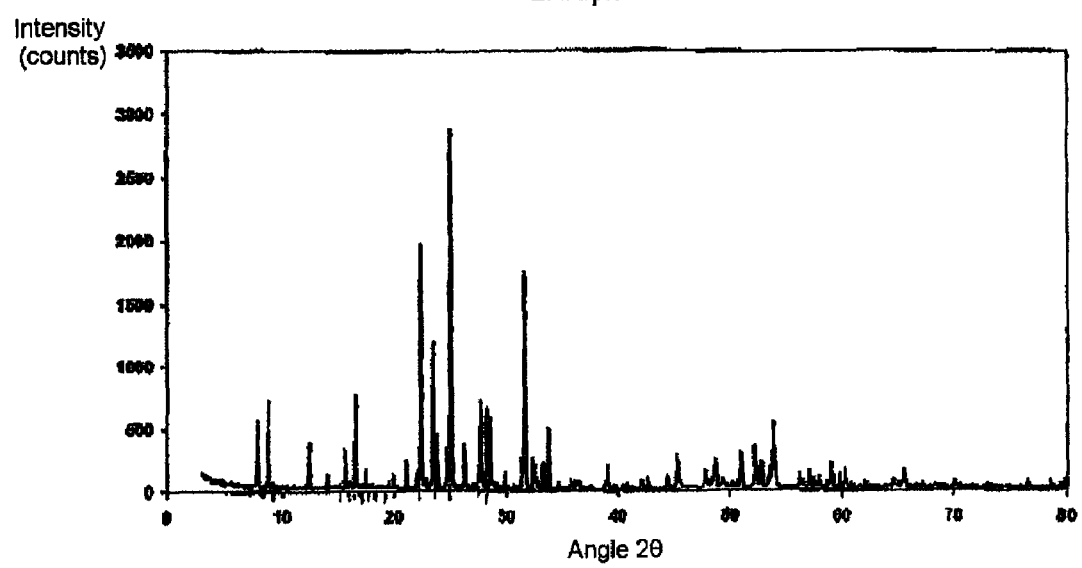

The solid obtained was washed in a solution of hydrogen peroxide (Alfa Aesar) containing 30% by weight diluted twice, for 4 hours, at ambient temperature. The solution was filtered and the solid recovered dried in the oven (110° C.) and then calcined for 2 hours in nitrogen at 600° C. (50 ml/min/g). The solid recovered was analyzed by X-ray diffraction (FIG. 7). The analysis confirmed that the desired phase was obtained, corresponding to the orthorhombic structure like the one described in the above publication with a small quantity of hexagonal phase. The solid obtained had the chemical formula $Mo_1V_{0.26}Te_{0.10}Nb_{0.14}O_z$.

Example 8

Preparation of a Phase with Antimony and Niobium of Composition $MoV_{0.28}Sb_{0.43}Nb_{0.15}O_w$.

MoVSbNbO catalyst containing a high concentration of phase B. The following were introduced into a flask: 1.99 g of ammonium metavanadate (GfE) and 45 ml of distilled water. The mixture was heated under reflux at 95° C. with stirring to obtain a clear solution, after which 1.24 g of antimony trioxide (Alfa Aesar)+10.00 g of ammonium heptamolybdate (Starck) were added. Heating was continued for one hour with argon blanket. A solution containing 2 ml of hydrogen peroxide (Alfa Aesar) containing 30% by weight for 10 ml of water was introduced. A clear orange solution was then obtained.

A mixture of niobic acid/oxalic acid with an oxalate/Nb ratio of 2.7 was prepared simultaneously. The following were introduced into a 50 ml beaker: 1.73 g of oxalic acid (Alfa Aesar), 0.76 g of niobic acid (CBMM) and 15 ml of distilled water. The mixture was heated at 70° C. with stirring until the initial solution became clear (about 4 hours). The solution was then centrifuged (3500 rpm for 15 minutes) and the liquid phase introduced into the solution containing the molybdenum, vanadium, and antimony. The mixture was stirred for half an hour and then placed in the oven at 110° C. for drying. The solid was precalcined in air at 320° C. for 4 hours (temperature ramp 2.5° C./min, flow rate=0 ml/min/g) and then calcined under purified nitrogen at 600° C. for 2 hours (temperature ramp 2.5° C./min, flow rate=50 ml/mn/g).

The solid recovered was analyzed by X-ray diffraction. This revealed a mixture of hexagonal phase and the desired orthorhombic phase. The solid obtained had the chemical formula $MoV_{0.3}Sb_{0.15}Nb_{0.1}O_w$.

Figure 8:
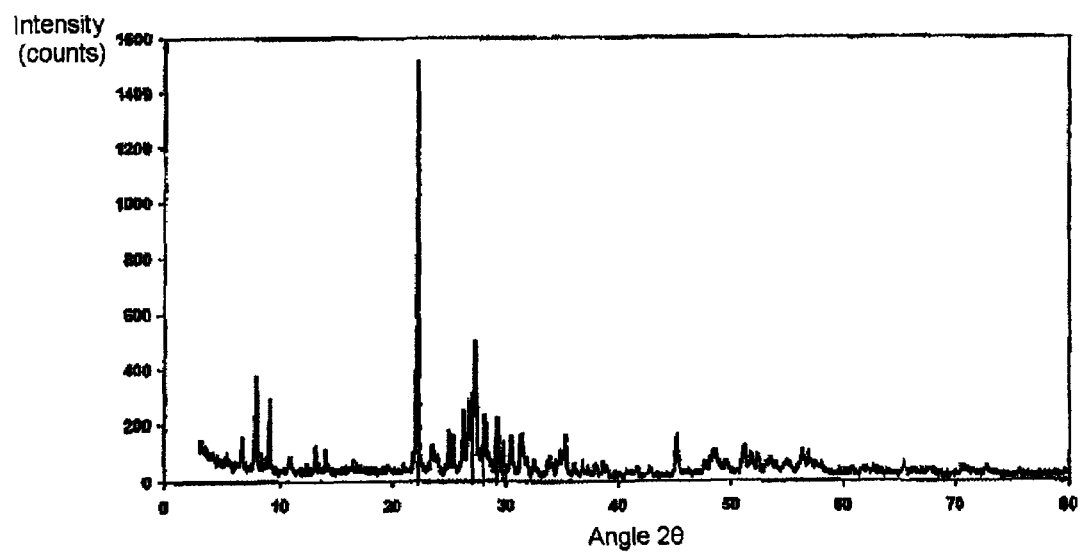

The solid obtained was washed in a solution of hydrogen peroxide (Alfa Aesar) containing 30% by weight diluted twice, for 4 hours, at ambient temperature. The solution was filtered and the solid recovered dried in the oven, then calcined for 2 hours in nitrogen at 600° C. (50 ml/min/g). The solid recovered was analyzed by X-ray diffraction (FIG. 8). The analysis confirmed the production of the desired phase, which corresponds to the orthorhombic structure. The solid had the composition $MoV_{0.28}Sb_{0.13}Nb_{0.15}O_w$.

Example 9

Preparation of a Phase with Tellurium and Molybdenum of the $TeMo_5O_{16}$ Type

Figure 9:
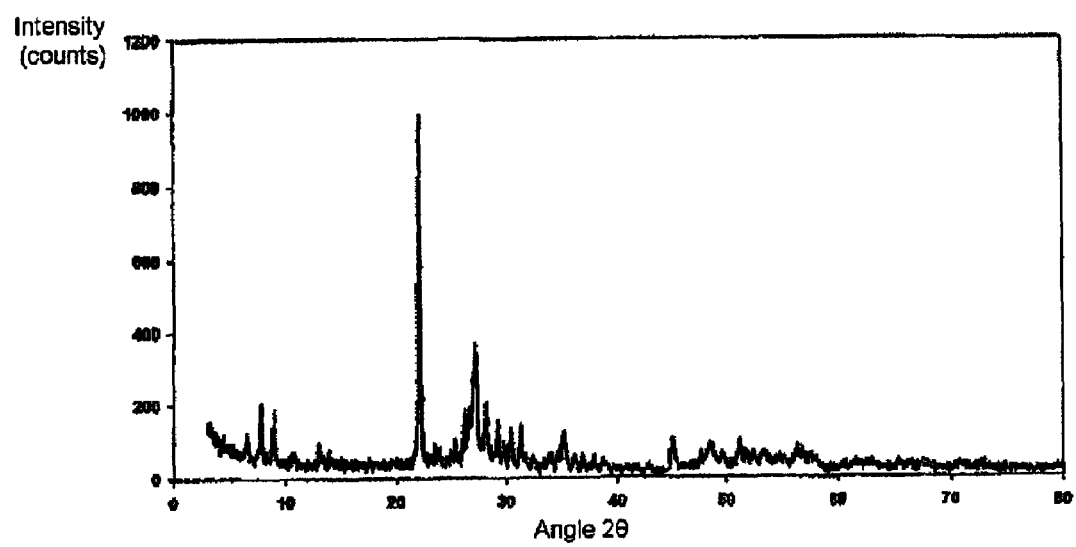

The $TeMo_5O_{16}$ phase was obtained by solid-solid reaction in a sealed ampoule under vacuum. 28.02 of g $MoO_3$ (Merck), 1.32 g of molybdenum metal (Alfa Aesar) and 6.65 g $TeO_2$ (Alfa Aesar) were ground together in an agate mortar for 15 minutes, until a uniform mixture was obtained. This mixture was introduced into a quartz ampoule. The ampoule was then sealed under vacuum and heated at 600° C. for 72 hours. The solid recovered was analyzed by X-ray diffraction (FIG. 9), and conformed to datasheet JCPDS 70-0451. The analysis confirmed the production of the desired phase, which corresponded to the monodinic structure having the chemical formula $MoTe_{0.2}O_x$.

Example 10

Preparation of a Phase of Composition $MoV_{0.23}Te_{0.09}Nb_{0.16}$ of a MoVTeNb Catalyst Containing a Large Amount of Phase B.

The following were introduced simultaneously into a 100 ml beaker: 35 ml of distilled water+7.78 g of ammonium heptamolybdate (Starck)+1.70 g of ammonium metavanadate (GfE)+2.22 g of telluric acid (Fluka). The mixture was heated at 80° C. with stirring until a clear red solution was obtained. This solution was allowed to cool at ambient temperature.

A solution of niobic acid/oxalic acid with an $O_x/Nb$ ratio of 2.70 was prepared simultaneously. The following were introduced into a 15 ml beaker: 10 ml of distilled water+0.82 g of niobic acid (CBMM)+1.67 g of oxalic acid (Alfa Aesar). The mixture was heated at 70° C. with stirring until the initial solution became clear (about 4 hours). This solution was centrifuged (3500 rpm for 15 minutes) and the liquid phase introduced into the clear red solution containing the molybdenum, vanadium and tellurium. After a few minutes, an opaque orange gel was obtained and placed in a crystallizer for drying overnight in the oven at 110° C. The solid was precalcined in air at 300° C. for 4 hours (50 ml/min/g) and then calcined under purified nitrogen at 600° C. for 2 hours (50 ml/min/g).

The solid recovered was analyzed by X-ray diffraction. This revealed a mixture of hexagonal phase and the desired orthorhombic phase. The solid obtained had a diffraction diagram similar to the one described in publication J. M. M. Millet, H. Roussel, A. Pigamo, J. L. Dubois, J. C. Jumas, Appl. Catal 232 (2002) 77-92, FIG. 1b. The solid obtained had the chemical formula $MoV_{0.3}Te_{0.2}Nb_{0.1}$.

Figure 10:
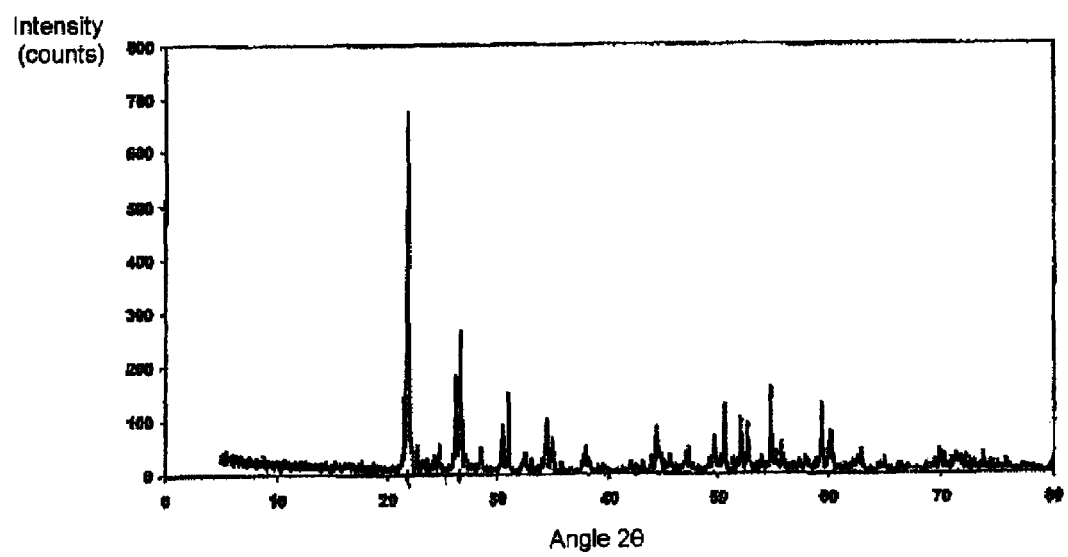

The solid obtained was washed in a solution of hydrogen peroxide (Alfa Aesar) containing 30% by weight diluted twice for 4 hours at ambient temperature. The solution was filtered and the solid recovered dried in the oven (at a 110° C.) and then calcined for 2 hours in nitrogen at 600° C. (50 mL/min/g). The solid recovered was analyzed by X-ray diffraction (FIG. 10). The analysis confirmed that the production of the desired phase, which corresponded to the orthorhombic structure as described in the above publication with a small quantity of hexagonal phase. The solid obtained had the chemical formula $Mo_1V_{0.23}Te_{0.09}Nb_{0.16}O_z$.

Example 11

Preparation of a Phase of Composition $MoV_{0.24}Te_{0.9}Nb_{0.16}$ of a MoVTeNb Catalyst Containing a Large Amount of Phase B.

The procedure described in Example 7 above was followed.

The following were introduced simultaneously into a 100 ml beaker: 35 ml of distilled water+7.78 g of ammonium heptamolybdate (Starck)+1.70 g of ammonium metavanadate (GfE)+2.22 g of telluric acid (Fluka). The mixture was heated at 80° C. with stirring to obtain a clear red solution. The solution was then left to cool at ambient temperature.

A solution of niobic acid/oxalic acid with an Ox/Nb ratio of 2.70 was prepared simultaneously. The following were introduced into a 50 ml beaker: 10 ml of distilled water+0.82 g niobic acid (CBMM)+1.67 g of oxalic acid (Alfa Aesar). The mixture was heated at 70° C. with stirring until the initial solution became clear (about 4 hours). This solution was centrifuged (3500 rpm for 15 minutes) and the liquid phase was then introduced into the clear red solution containing the molybdenum, vanadium and tellurium. After a few minutes, an opaque orange gel was obtained, and was placed in a crystallizer for drying overnight in the oven at 110° C. The solid was precalcined in air at 300° C. for 4 hours (50 ml/min/g) and then calcined in purified nitrogen at 600° C. for 2 hours (50 ml/min/g).

The solid recovered was analyzed by X-ray diffraction. This revealed a mixture of hexagonal phase and of the desired orthorhombic phase. The solid obtained had a diffraction diagram similar to the one described in publication J. M. M. Millet, H. Roussel, A. Pigamo, J. L. Dubois, J. C. Jumas, Appl. Catal 232 (2002) 77-92, FIG. 1b. The solid obtained had the chemical formula $MoV_{0.3}Te_{0.2}Nb_{0.1}$.

The solid obtained was washed in a solution of hydrogen peroxide (Alfa Aesar) containing 30% by weight diluted twice, for 4 hours, at ambient temperature. The solution was filtered and the solid recovered dried in the oven (110° C.) and then calcined for 2 hours in nitrogen at 600° C. (50 ml/min/g). The solid recovered was analyzed by X-ray diffraction. The analysis confirmed that the desired phase was obtained, corresponding to the orthorhombic structure like the one described in the above publication with a small quantity of hexagonal phase. The solid obtained had the chemical formula $MoV_{0.24}Te_{0.09}Nb_{0.16}$.

Catalyst Test

Example 12

The pure phases thus prepared were tested as follows: 0.5 to 1.5 g of solid was introduced into a straight fixed-bed Pyrex reactor and the temperature ramp (2.5° C./min) was carried out under nitrogen. When the desired temperature was reached, the following reaction mixture conditions were obtained: total flow rate 30 ml/min (5% $C_3H_8$, 5% Ne, 10% $O_2$, 45% $H_2O$ and 35% $N_2$ (molar percent)) and the reactor was allowed to stabilize for 30 minutes. A 25 ml flask containing 5 ml of water was placed at the reactor outlet to allow the organic compounds to condense. For each temperature, the condensation time was 2 hours. Incondensables were analyzed in line by a Chrompack chromatograph and the liquid effluents were analyzed after reaction on another Chrompack chromatograph.

Figure 11:
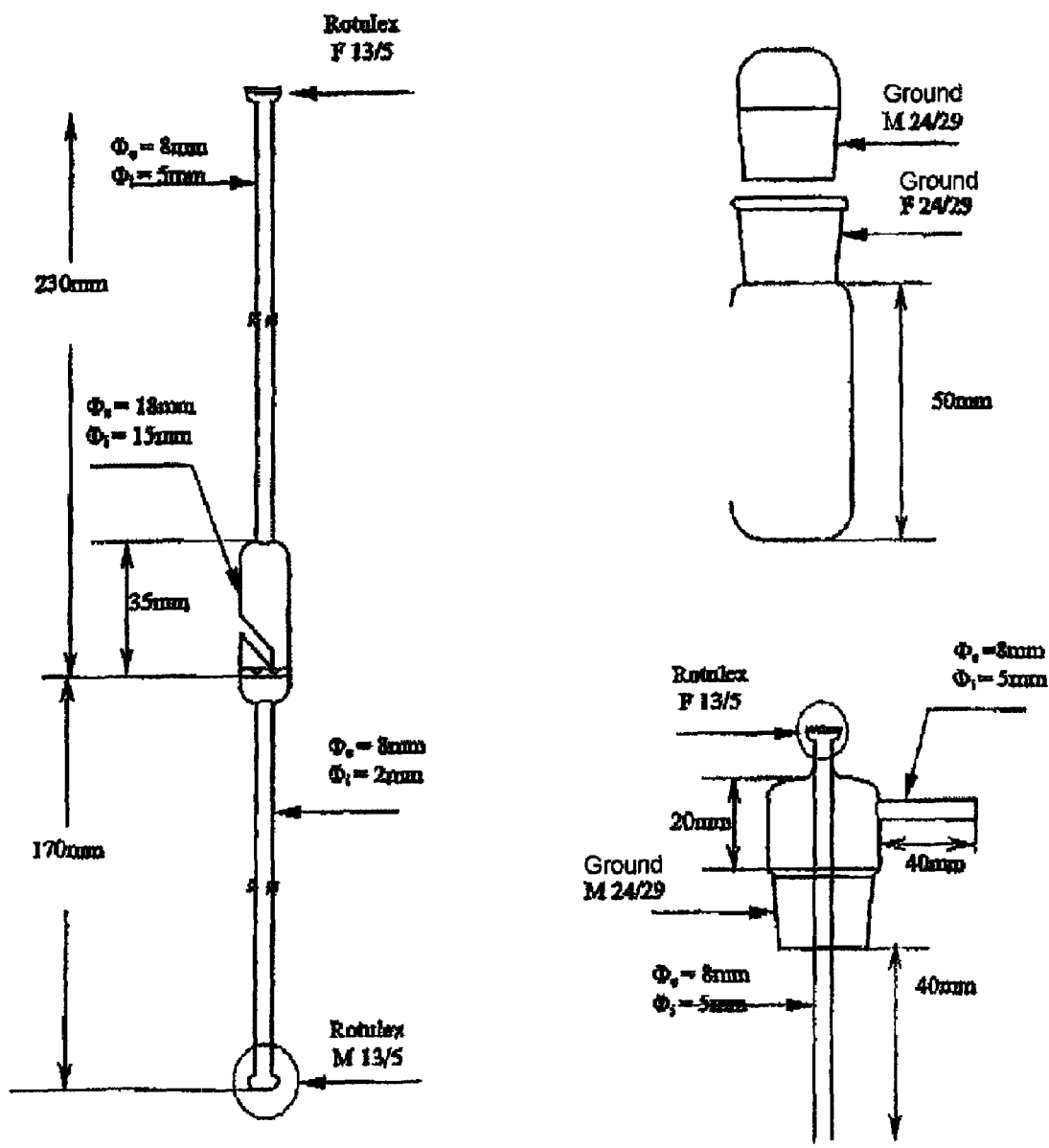

A diagram of the reactor is appended (FIG. 11).

Example 13

To perform the tests of the catalyst 10 and 11: tests A1, A2, AA1, AA2 under the same conditions of tests I and J of catalyst 7, a mass of 0.5 g was used for the tests A1 and AA1, and a mass of 0.47 g was used for the tests A2 and AA2. The results obtained are given in Table 2. The results indicate very good reproducibility of catalyst performance.

TABLE 1

Table of mechanical mixtures of phases (mass of each solid in the mixture): Mass of solid in the column (solid C) + mass of solid on the line (solid L). The letter indicated in the table corresponds to the numeral of the test example.

| Mixture: Solid C + Solid L | 1 | 2 | 3 | 4 | 5 | 6 | 7 | 8 | 9 | 10 | 11 |
|---|---|---|---|---|---|---|---|---|---|---|---|
| 1 | D: 1 g | | | | | | | | | | |
| 2 | | E: 1 g | | | | | | | | | |
| 3 | | | F: 1 g | | | | | | | | |
| 4 | T: 0.5 + 0.5 g | | | G: 1 g | | | | | | | |
| 5 | P: 0.5 + 0.5 g Y: 0.5 + 0.1 g Z: 0.5 + 0.25 g | Q: 0.5 + 0.5 g | | | | B: 0.5 g | | | | | |
| 6 | | | | | | R: 0.5 + 0.5 g | C: 1 g | | | | |
| 7 | M: 0.5 + 0.5 g X: 0.4 + 0.1 g W: 0.5 + 1 g | O: 0.5 + 0.5 g | S: 0.5 + 0.5 g | | | | N: 0.5 + 0.5 g | I: 0.5 g J: 0.47 g | | | |
| 8 | L: 0.5 + 0.5 g | | | | | | | | H: 0.5 g | | |
| 9 | | | | | U: 0.5 + 0.5 g | V: 0.5 + 0.5 g | | | | K: 1 g | |
| 10 | M: 0.5 + 0.5 g | O: 0.5 + 0.5 g | | | | | N: 0.5 + 0.5 g | | | A1: 0.5 A2: 0.47 | |
| 11 | | | | | | | | | | | AA1: 0.5 AA2: 0.47 |

Example D: 1 g of solid of example 1 was fed to a reactor. The solid was heated under nitrogen to the desired temperature. The catalyst was then placed in the reaction mixture: total flow rate=30 ml/min. (5% Ne, 10% $O_2$, 35% $N_2$, 45% $H_2O$ and 5% $C_3H_8$). Examples B, C and E to K: a mass m (specified in the table) of the solids prepared in examples 2 to 9 was fed to the reactor as in example D, and the catalyst was tested as in example D.

Examples L to Y and Z: two masses $m_1$ and $m_2$ of two different solids were mixed in an agate mortar for 15 minutes to obtain a uniform mixture. The mixture thus formed was fed to a reactor as in example D, and the catalyst was tested as in example D.

TABLE 2

Results (comparative: pure phases - use of a single catalyst)

| Test | Catalyst Ex. | m. catal. (g) | T° reaction | Conversions (in %) C$_3$H$_8$ | O$_2$ | CO | CO$_2$ | C$_3$H$_6$ | acrolein | acetone | acetic acid | propionic acid | acrylic acid | Balances (%) C | O |
|---|---|---|---|---|---|---|---|---|---|---|---|---|---|---|---|
| Ex. A1 | 10 | 0.5 | 355 | 28.3 | 36.0 | 7.2 | 13.6 | 9.2 | 0.0 | 1.8 | 9.0 | 0.5 | 58.7 | 100 | 101 |
|  |  |  | 388 | 39.9 | 57.8 | 12.9 | 19.1 | 6.3 | 0.0 | 0.5 | 7.3 | 0.2 | 53.6 | 100 | 97 |
| Ex. A2 |  | 0.47 | 323 | 9.5 | 9.7 | 2.7 | 7.3 | 23.5 | 0.2 | 3.2 | 7.4 | 2.0 | 53.8 | 98 | 97 |
|  |  |  | 355 | 20.3 | 24.3 | 4.3 | 13.3 | 16.7 | 0.1 | 0.9 | 6.0 | 0.5 | 58.3 | 101 | 100 |
|  |  |  | 387 | 34.5 | 47.2 | 11.3 | 17.1 | 9.3 | 0.0 | 0.3 | 5.3 | 0.2 | 56.5 | 101 | 100 |
| Ex. B | 5 | 0.5 | 322 | 4.1 | 5.1 | 14.3 | 17.7 | 31.5 | 0.1 | 1.6 | 32.1 | 0.3 | 2.6 | 98 | 99 |
|  |  |  | 353 | 8.1 | 11.6 | 19.0 | 23.8 | 23.5 | 0.1 | 0.7 | 29.6 | 0.1 | 3.0 | 99 | 99 |
|  |  |  | 385 | 14.1 | 22.6 | 25.4 | 29.2 | 17.6 | 0.1 | 1.3 | 23.0 | 0.1 | 3.2 | 100 | 98 |
|  |  |  | 407 | 18.8 | 32.5 | 29.7 | 33.1 | 14.1 | 0.2 | 0.1 | 19.4 | 0 | 3.5 | 98 | 97 |
| Ex. C | 6 | 1 | 380 | 0.0 | 0.0 | 0.0 | 0.0 | 0.0 | 0.0 | 0.0 | 0.0 | 0.0 | 0.0 | 100 | 100 |
| Ex. D | 1 | 1 | 380 | 0.0 | 0.0 | 0.0 | 0.0 | 0.0 | 0.0 | 0.0 | 0.0 | 0.0 | 0.0 | 100 | 100 |
| Ex. E | 2 | 1 | 381 | 1.7 | 1.5 | 0.0 | 8.3 | 49.4 | 0.3 | 0.3 | 3.6 | 0.0 | 38.0 | 100 | 100 |
| Ex. F | 3 | 1 | 380 | 0.0 | 0.0 | 0.0 | 0.0 | 0.0 | 0.0 | 0.0 | 0.0 | 0.0 | 0.0 | 100 | 100 |
| Ex. G | 4 | 1 | 350 | 20.5 | 32.9 | 30.1 | 35 | 11.1 | 0.2 | 0.1 | 15.3 | 0.1 | 8.0 | 98 | 101 |
|  |  |  | 380 | 32.1 | 61.4 | 30.8 | 40.5 | 8.7 | 0.2 | 0.3 | 11.4 | 0.1 | 8.0 | 100 | 101 |
| Ex. H | 8 | 0.5 | 391 | 44.6 | 66.5 | 9.8 | 21.1 | 7.8 | 0.0 | 0.4 | 12.9 | 0.2 | 47.8 | 101 | 102 |
| Ex. I | 7 | 0.5 | 386 | 39.6 | 56.6 | 9.2 | 17.2 | 7.7 | 0.0 | 0.3 | 8.4 | 0.2 | 57.1 | 97 | 99 |
| Ex. J | 7 | 0.47 | 329 | 10.5 | 10.7 | 3.0 | 4.9 | 24.2 | 0.0 | 5.7 | 8.9 | 1.7 | 51.5 | 100 | 100 |
|  |  |  | 356 | 19.2 | 22.5 | 5.2 | 7.9 | 17.1 | 0.0 | 1.4 | 9.0 | 0.7 | 58.7 | 99 | 99 |
|  |  |  | 392 | 32.9 | 39.8 | 8.9 | 16.3 | 10.8 | 0.0 | 0.4 | 7.8 | 0.2 | 55.5 | 99 | 99 |
|  |  |  | 406 | 37.8 | 54.9 | 10.6 | 20.3 | 9.4 | 0.3 | 0.0 | 7.2 | 0.2 | 52.1 | 99 | 100 |
| Ex. K | 9 | 1 | 380 | 0.0 | 0.0 | 0.0 | 0.0 | 0.0 | 0.0 | 0.0 | 0.0 | 0.0 | 0.0 | 100 | 100 |
| Ex. AA1 | 11 | 0.5 | 390 | 40.6 | 59.2 | 10.8 | 24.7 | 6.9 | 0.0 | 0.1 | 3.8 | 0.1 | 53.6 | 100 | 100 |
| Ex. AA2 |  | 0.47 | 323 | 10.0 | 11.2 | 3.5 | 10.5 | 20.5 | 0.1 | 1.7 | 11.0 | 1.2 | 51.5 | 100 | 98 |
|  |  |  | 354 | 18.6 | 22.9 | 5.0 | 13.6 | 13.9 | 0.1 | 0.7 | 8.8 | 0.5 | 57.3 | 100 | 99 |
|  |  |  | 386 | 33.7 | 47.7 | 9.4 | 21.0 | 8.9 | 0.0 | 0.2 | 5.9 | 0.1 | 54.5 | 100 | 99 |

TABLE 3

Mechanical mixtures 0.5 g + 0.5 g unless specified

| Test | Catalyst Ex. | m. catal. (g) | T° reaction | Conversions (in %) C$_3$H$_8$ | O$_2$ | CO | CO$_2$ | C$_3$H$_6$ | acrolein | acetone | acetic acid | propionic acid | acrylic acid | Balances (%) C | O |
|---|---|---|---|---|---|---|---|---|---|---|---|---|---|---|---|
| Ex. L | 1 + 8 | 1 | 393 | 37.3 | 53.0 | 8.4 | 18.0 | 9.3 | 0.0 | 0.2 | 4.4 | 0.2 | 59.4 | 100 | 100 |
| Ex. M | 1 + 7 | 1 | 390 | 44.2 | 60.3 | 7.0 | 12.9 | 7.0 | 0.0 | 0.2 | 5.3 | 0.2 | 67.4 | 99 | 100 |
|  |  |  | 355 | 35.7 | 43.5 | 3.4 | 5.9 | 8.5 | 0.0 | 0.8 | 8.3 | 0.7 | 72.5 | 101 | 103 |
|  |  |  | 323 | 21.1 | 23.6 | 2.3 | 3.0 | 12.4 | 0.0 | 2.6 | 7.4 | 2.3 | 69.9 | 101 | 103 |
| Ex. N | 6 + 7 | 1 | 387 | 44.4 | 63.1 | 8.3 | 16.7 | 7.3 | 0.0 | 0.2 | 6.5 | 0.2 | 60.8 | 98 | 99 |
| Ex. O | 2 + 7 | 1 | 390 | 45.3 | 62.9 | 7.3 | 14.2 | 6.5 | 0.0 | 0.2 | 5.4 | 0.2 | 66.2 | 99 | 100 |
| Ex. P | 1 + 5 | 1 | 384 | 6.1 | 8.2 | 10.9 | 21.4 | 23.7 | 0.1 | 0.3 | 8.2 | 0.2 | 35.2 | 100 | 100 |
| Ex. Q | 2 + 5 | 1 | 383 | 11.6 | 18.7 | 17.9 | 30.3 | 14.4 | 0.1 | 0.2 | 9.9 | 0.2 | 27.0 | 99 | 99 |
| Ex. R | 6 + 5 | 1 | 383 | 9.7 | 15.6 | 17.2 | 30.7 | 15.7 | 0.2 | 0.2 | 10.3 | 0.2 | 25.5 | 99 | 99 |
| Ex. S | 3 + 7 | 1 | 389 | 36.6 | 51.5 | 8.7 | 17.1 | 9.8 | 0.0 | 0.4 | 11.2 | 0.2 | 52.4 | 97 | 99 |
| Ex. T | 1 + 4 | 1 | 350 | 9.6 | 10.2 | 6.0 | 9.7 | 29.2 | 0.1 | 0.9 | 9.9 | 0.7 | 43.4 | 101 | 101 |
|  |  |  | 380 | 16.6 | 21.5 | 10.0 | 20.3 | 21.2 | 0.0 | 0.4 | 9.2 | 0.3 | 38.6 | 99 | 101 |
| Ex. U | 9 + 4 | 1 | 326 | 12.9 | 21.2 | 6.1 | 46.8 | 16.9 | 0.1 | 0.3 | 19.0 | 0.7 | 10.0 | 102 | 101 |
|  |  |  | 357 | 19.4 | 30.5 | 15.8 | 37.0 | 15.7 | 0.1 | 0.4 | 19.4 | 0.4 | 11.4 | 99 | 99 |
|  |  |  | 378 | 28.2 | 46.9 | 22.8 | 37.5 | 12.8 | 0.0 | 0.3 | 15.9 | 0.1 | 10.5 | 100 | 97 |
| Ex V | 9 + 5 | 1 | 383 | 6.1 | 8.9 | 17.3 | 23.9 | 19.9 | 0.2 | 0.2 | 5.6 | 0.1 | 32.7 | 101 | 96 |
| Ex W | 1 (67%) + 7 (33%) | 1.5 | 353 | 31.3 | 36.9 | 3.3 | 5.7 | 10.8 | 0.0 | 0.7 | 5.0 | 0.8 | 73.7 | 99 | 99 |
|  |  |  | 386 | 38.0 | 52.8 | 5.0 | 10.5 | 8.6 | 0.0 | 0.2 | 3.5 | 0.3 | 72.0 | 100 | 100 |
| Ex. X | 1 (20%) + 7 (80%) (0.1 g + 0.4 g) | 0.5 | 387 | 25.1 | 30.4 | 2.2 | 11.1 | 14.9 | 0.0 | 0.6 | 8.1 | 0.3 | 64.9 | 99 | 97 |
|  |  |  | 408 | 36.2 | 50.7 | 9.4 | 17.6 | 10.1 | 0.3 | 0.6 | 6.3 | 0.1 | 56.3 | 98 | 99 |
| Ex. Y | 1 (17%) + 5 (83%) | 0.6 | 320 | 4.2 | 5.5 | 11.8 | 19.0 | 25.2 | 0.0 | 1.8 | 28.4 | 0.8 | 13.0 | 99 | 99 |
|  |  |  | 352 | 7.1 | 10.2 | 16.5 | 23.3 | 22.3 | 0.1 | 0.6 | 17.0 | 0.4 | 20.0 | 100 | 99 |
|  |  |  | 383 | 11.8 | 18.9 | 19.7 | 29.2 | 14.7 | 0.0 | 0.2 | 13.5 | 0.2 | 22.6 | 99 | 100 |
|  |  |  | 407 | 17.8 | 31.6 | 24.3 | 37.4 | 12.6 | 0.1 | 0.0 | 10.6 | 0.1 | 14.8 | 99 | 98 |
| Ex. Z | 1 (33%) + 5 (67%) | 0.75 | 323 | 4.3 | 5.7 | 11.9 | 20.5 | 25.6 | 0.1 | 1.6 | 25.5 | 0.7 | 14.1 | 98 | 101 |
|  |  |  | 352 | 5.8 | 8.4 | 16.9 | 23.0 | 20.1 | 0.2 | 0.6 | 14.5 | 0.4 | 24.4 | 98 | 99 |
|  |  |  | 385 | 10.1 | 16.3 | 19.0 | 30.4 | 16.3 | 0.2 | 0.2 | 9.1 | 0.1 | 24.9 | 99 | 100 |
|  |  |  | 407 | 16.5 | 28.9 | 23.4 | 36.2 | 11.8 | 0.1 | 0.2 | 8.2 | 0.1 | 20.2 | 100 | 100 |

The invention claimed is:

1. A method for preparing acrylic acid from propane, characterized in that a gas mixture comprising propane, steam and, optionally, an inert gas and/or molecular oxygen, is passed over a catalyst conferring good selectivity, comprising a crystalline catalyst phase:
satisfies the formula (I):

$$Te_a Mo_1 V_b Nb_c O_x \quad (I)$$

in which
a is between 0.1 and 2 limits included;
b is between 0 and 1 limits included;
c is between 0 and 0.2 limits included;
  x and y represent the quantity of oxygen bound to the other elements and depends on their oxidation states, and corresponds to a hexagonal lattice structure of which the X-ray diffraction spectrum, diffraction angles (2θ) measured using the copper Kα$_1$ and Kα$_2$ lines as an X-ray source, with a 0.02° step, has a peak at the diffraction angle 28.2° and lattice parameters a=0.729 (±0.02) nm×p, p being an integer from 1 to 4; c=0.400 (±0.01) nm×q, q being an integer from 1 to 2; α=90°, Y=120°,
  or of a monoclinic structure $Te_2MoO_7$ or $Te_{0.2}MoO_x$, combined with a crystalline catalyst phase for activating the propane.

2. A method as claimed in claim 1, characterized in that the crystalline catalyst phase for activating the propane comprises mixed metal oxides of formulae (II), (II') or (II"):

$$Mo_d V_e O_y \quad (II)$$

$$Mo_{d'} V_f Sb_g Nb_h O_w \quad (II')$$

$$Mo_{d''} V_j Te_j Nb_k O_z \quad (II'')$$

in which
d, d' and d" are between 0.93 and 1 limits included;
e is between 0.05 and 1 limits included;
f is between 0 and 0.5 limits included;
g is between 0.05 and 0.3 limits included;
h is between 0.01 and 0.2 limits included;
i is between 0 and 0.5 limits included;
j is between 0.05 and 0.3 limits included;
k is between 0.01 and 0.2 limits included;
v, w and z represent the quantity of oxygen bound to the other elements and depends on their oxidation states,
  it being understood that the product of formula (II') has either a hexagonal lattice structure in which the X-ray diffraction spectrum has a peak at the diffraction angle 28.2°, and lattice parameters a=0.729 (±0.02) nm×p, p being an integer from 1 to 4; c=0.400 (±0.01) nm×q, q being an integer from 1 to 2; α=90°, γ=120°, or has an orthorhombic lattice structure in which the X-ray diffraction spectrum has a peak at the diffraction angle 27.3° and lattice parameters a=2.68 (±0.04) nm; b=2.12 (±0.04) nm; c=0.401 (±0.006) nm×q', q' being an integer from 1 to 2; α=β=γ=90°, and it being understood that the product of formula (II") has an orthorhombic lattice structure and also has an X-ray diffraction peak at the diffraction angle 27.3° and lattice parameters a=2.68 (±0.04) nm; b=2.12 (±0.04) nm; c=0.401 (±0.006) nm×q', q' being an integer from 1 to 2; α=β=γ=90°.

3. A method as claimed in either of claims 1 and 2, characterized in that a gas mixture comprising propane, steam and, optionally, an inert gas and/or molecular oxygen, is passed over a catalyst conferring a good selectivity of formula (I) defined in claim 1, or of a monoclinic structure $Te_2MoO_7$ or $Te_{0.2}MoO_x$ combined with a crystalline catalyst phase for activating the propane in ratios from 90/10 to 15/85 by weight of the total weight of mixture, of the catalyst conferring good selectivity/catalyst for activating the propane.

4. A method as claimed in one of claims 1 to 3, characterized in that a gas mixture comprising propane, steam and, optionally, an inert gas and/or molecular oxygen, is passed over a catalyst conferring a good selectivity of formula (I) defined in claim 1, or of a monoclinic structure $Te_2MoO_7$ or $Te_{0.2}MoO_x$ combined with a crystalline catalyst phase for activating the propane in ratios from 90/10 to 50/50 by weight of the total weight of mixture, of the catalyst conferring good selectivity/catalyst for activating the propane.

5. A method as claimed in one of claims 1 to 4, characterized in that a gas mixture comprising propane, steam and, optionally, an inert gas and/or molecular oxygen, is passed over a catalyst conferring a good selectivity of formula (I) defined in claim 1, or of a monoclinic structure $Te_2MoO_7$ or $Te_{0.2}MoO_x$ combined with a crystalline catalyst phase for activating the propane in ratios from 70/30 to 50/50 by weight of the total weight of mixture, of the catalyst conferring good selectivity/catalyst for activating the propane.

6. A method as claimed in either of claims 1 and 2, characterized in that, when operating in the presence of molecular oxygen, the propane/molecular oxygen molar ratio in the initial gas mixture is equal to or greater than 0.3.

7. A method as claimed in claim 6, characterized in that the propane/molecular oxygen molar ratio in the initial gas mixture is equal to or greater than 0.5.

8. A method as claimed in either of claims 1 and 2, in which the molar proportions of the components of the initial gas mixture are:
propane/O$_2$/inert gas/H$_2$O (steam)=1/0.05-3/1-10/1-10.

9. A method as claimed in claim 8, in which the molar proportions of the components of the initial gas mixture are:
propane/O$_2$/inert gas/H$_2$O (steam)=1/0.05-2/1-10/1-10.

* * * * *